United States Patent [19]

Kosasky

[11] Patent Number: 4,779,627
[45] Date of Patent: Oct. 25, 1988

[54] PROCESS AND APPARATUS FOR DETERMINING FEMALE OVULATION TIME BY MEASUREMENT OF SALIVA VISCOELASTICITY

[75] Inventor: Harold J. Kosasky, Chestnut Hill, Mass.

[73] Assignee: The Academy of Applied Sciences, Inc., Boston, Mass.

[21] Appl. No.: 849,162

[22] Filed: Apr. 4, 1986

[51] Int. Cl.$^4$ ............................................. G01N 33/16
[52] U.S. Cl. ......................................... 128/738; 73/53
[58] Field of Search ....................... 128/630, 738, 760; 73/54, 60

[56] References Cited

U.S. PATENT DOCUMENTS

| | | | |
|---|---|---|---|
| 3,982,423 | 9/1976 | Schuster | 73/54 |
| 4,002,056 | 1/1977 | Kopito et al. | 73/53 |
| 4,072,045 | 2/1978 | Kopito | 73/54 |

OTHER PUBLICATIONS

L. E. Kopito et al, "The Tackiness Rheometer Determination of the Viscoelasticity of Cervical Mucus", *Human Ovulation*, Elsevier/North-Holland Biomedical Press, 1979, pp. 351–361.
Gerald Oster, et al, "Cyclic Variation of Sialic Acid Content in Saliva", *American Journal of Obstetrics and Gynecology*, vol. 114, No. 2, Sep. 15, 1972, pp. 190–193.
Ira L. Shannon et al, "Saliva: Composition and Secretion", *Monographs in Oral Science*, vol. 2, 1974.

*Primary Examiner*—Edward M. Coven
*Assistant Examiner*—Randy Citrin
*Attorney, Agent, or Firm*—Rines and Rines Shapiro and Shapiro

[57] ABSTRACT

Viscoelastic measurements of sublingual saliva thinning minimums are employed reliably to determine the approach of ovulation in females and other related hormonal and rheological functions.

10 Claims, 2 Drawing Sheets

PROCESS AND APPARATUS FOR DETERMINING FEMALE OVULATION TIME BY MEASUREMENT OF SALIVA VISCOELASTICITY

The present invention relates to the determination of the time of ovulation through the monitoring of the viscoelasticity or tackiness of the female saliva; being also useful for determination of hormonal and related functions associated with ovulation, and conversely with similarly determining the non-ovulation effectiveness of oral contraceptives and the like.

It has earlier been known that the cervical mucus of a female has a minimum thinness or highest fluidity just before ovulation and closely coincident with the surge in estradiol and in the luteinizing hormone (LH) peak—a phenomenon that led to my previous activities in the development of techniques for monitoring the viscoelasticity and other properties of cervical mucus as a predictor of time of ovulation, and the improvements in rheometer or viscometer apparatus for measuring such viscoelastic properties (L. E. Kopita and H.J. Kosasky, "The tackiness rheometer determination of the viscoelasticity of cervical mucus", *Human Ovulation*, edited by E.S.E. Hafez, Elsevier, North-Holland Biomedical Press, 1979, commencing with p. 351, on; and U.S. Pat. No. 4,002,056). Though the viscoelasticity of the cervical mucus has several small dips in its characteristic curve of viscosity versus time preceding, during and following ovulation (a four-day period), there is a distinct identifiable minimum coincident with the peaking of estradiol, representing the thinning of bodily secretions. Instruments designed to measure this effect are described in, for example, said Letters Patent and in U.S. Pat. No. 4,072,045.

While this is a most desirable technique for monitoring ovulation times and related hormonal and rheologic property functions, it requires the insertion of cervical mucus sampling applicators into the vagina, which is an impediment to universal usage, has features of discomfort, demands sanitation, and requires proper positioning of the central portion of the cervix. the non-observable aspiration or extraction of the hoped-for cervical mucus, moreover, can result in the withdrawal of undesired vaginal fluids that can upset reliable measurements. Additionally, the mucus is of relatively high viscosity (5000-50,000 centipoise), requiring one-use sampling surfaces in viscometers used to measure the viscoelasticity of the mucus.

Saliva and other body fluids have been known to undergo chemical changes during the menstrual cycle (for example, G. Oster, et al, "Cyclic variation of sialic acid content in saliva", Am. J. Obstet Gynercol, Vol. 114, No. 2, p. 190, Sept. 15, 1972, and I. Shannon, "Saliva: Composition and Secretion", 1974. Until the discovery underlying the present invention, however, the unique reproducible and single minimum viscosity dip characteristic of saliva during the ovulation cycle was apparently not detected—the saliva cycle, indeed, being restricted to about two days as compared with four days for cervical mucus, and having a viscosity range but 1/10 to 1/100 of that of cervical mucus, and thus understandably difficult to detect, particularly with cervical mucus instruments.

I have now discovered, indeed, that particularly sublingual saliva (which has been noted to have less water than saliva from other parts of the mouth, and about 50% mucus, as contrasted with over 70–90% water in submandibular saliva) produces a unique and reliably measurable minimum dip in viscoelasticity or tackiness that is coincident with the ovulation cycle and its surge of estradiol, and also tracks the minimum dip in cervical mucus viscoelasticity, though it is much narrower (48 hrs, vs. 4 days) and far below the viscosity levels of such mucus, as before stated. The use of saliva, furthermore, totally obviates the difficulties and disadvantages associated with the extraction of cervical mucus from the vagina, and thus promises to be widely and universally acceptable as an ovulation monitor, and most simply useable by even the less educated, as well.

An object of the present invention, accordingly, is to provide a new and improved process for determining the time of ovulation and related hormone functions of a female that, though based on female fluid viscosity measurements, is not subject to the before-described and other limitations of cervical mucus viscoelasticity measurements, nor the more undesirable blood hormone measurements or other chemical measurements, but employs a simpler and distinctly unique minimum saliva tackiness phenomenon as a much improved alternative.

A further object is to provide a novel apparatus for the same.

Other and further objects will be explained hereinafter and are more particularly delineated in the appended claims.

In summary, from one of its important viewpoints, the invention embraces a process for determining the time of ovulation of a female, that comprises, extracting a sample of saliva from the mouth of the female; compressing the sample between opposing surfaces sufficiently finely roughened to cause adherence of the saliva to the same; applying a predetermined relative pulling or shearing force between said surfaces correspondingly to stretch the saliva, the amount of stretch providing a measure of the degree of viscoelasticity under such predetermined force; comparing the measured degree of viscoelasticity with a predetermined unique monthly minimum dip of viscoelasticity in the saliva of the female; and indicating near and substantial coincidence of the measured degree of viscoelasticity with said minimum dip to indentify that the time of mid-cycle of ovulation is about to occur. Preferred details and best mode embodiments are later discussed.

The invention will now be described with reference to the accompanying drawing,

FIG. 1 of which is a graph (viscosity plotted in units of centipoise along the ordinate, being plotted logarithmically for cervical mucus and linearly for saliva, and as a function of time in days plotted along the abscissa) showing the phenomenon of conincidence of a unique sublingual saliva viscosity minimum with proximal ovulation, employed in the process of the invention, and compared with a similar phenomenon with cervical mucus, but occurring over a much narrower time span and over a small fraction of the viscosity range involved with cervical mucus;

Figures 1, 2:
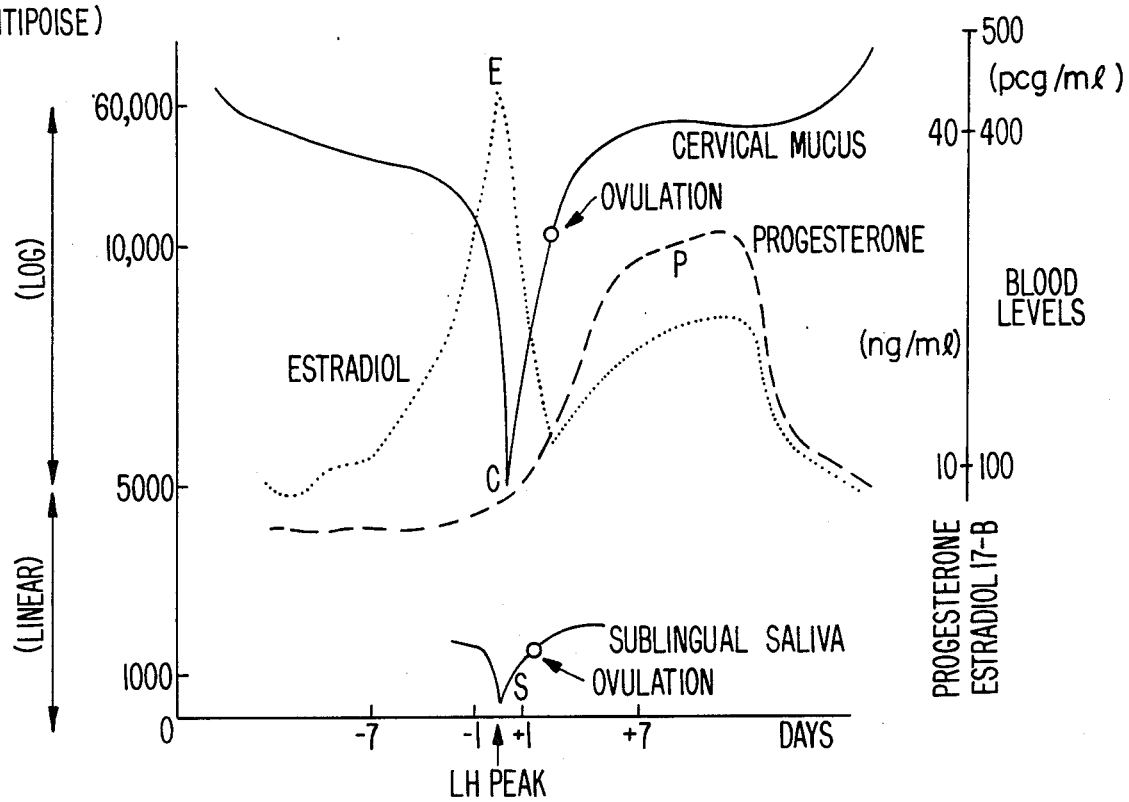
FIG. 2 is an enlarged graph of the saliva characteristic of FIG. 1.

Referring to FIG. 1, underlying the invention, as before stated, is the discovery that quantitatively, reliably and reproducibly, the viscoelasticity of particularly sublingual saliva goes through a unique minimum S (bottom graph) at the mid-cycle, coincident with the peaking surge in estradiol E, and somewhat paralleling the cervical mucus dip C, (upper plot) though with the saliva being relatively watery (30 to 1500 centipoise) as compared with the 5000-50,000 centipoise viscosity range of cervical mucus.

The coincidence with the peak of luteinizing hormone "LH Peak" and the following progesterone post-ovulation development P is also shown in FIG. 1 (plotted along the right-hand ordinate in units of ng/ml).

As shown in FIG. 1 and as previously delineated, the cercival mucus viscoelastic characteristic curve dip and rise extends over a period of about 4 days, with the actual ovulation occurring within a day and a half of the minimum dip C. The sublingual saliva characteristic falls much more steeply and extends over a period of about 48 hours, with ovulation occurring within 24 hours of the minimum S. The measurements of the cervical mucus were taken with the rheometer equipment described in my said *Human Ovulation* article; and the saliva measurements were made with a modified rotary type eccentric glass cylinder rheometer having randomly roughened opposing surfaces (of the order of 10-20 thousandths of an inch) and with saliva samples of about 0.25 mm in thickness.

In the normal ovulating woman, typical cervical mucus confirmatory patterns C have been observed, with viscoelasticity beginning to decrease, FIG. 1, three days before the LH peak to minimal values C. Within one to two days after the LH peak, the viscosity has risen to the pre-ovulatory levels, but than may dip again, as shown to the right, but not as low as the minimum C. The decreasing viscoelasticity in saliva, as before stated, has been found to have a shorter or narrower time span and usually without subsequent dips (or earlier dips) as may occur with cervical mucus. The minimum thinness at S represents the time of maximum sperm penetration, so that advent of the commencement of the saliva viscoelasticity dip, signals the approach of an appropriate time for conception.

This coincidence with mid-cycle, moreover, has been confirmed with blood tests, the levels of which are calibrated along the right-hand ordinate (pcg/ml), FIGS. 1 and 2.

The viscoelasticity of the saliva thus correlates with the hormonal relationship of the menstrual cycle, with midcycle and the LH peak, and then rises to the preovulatory levels.

Sublingual saliva was examined 1295 times in 73 patients through 206 cycles. 831 samples of cervical mucus and sublingual saliva were each obtained daily from 25 women in 112 cycles, who were taking oral progestogens. In 60% of the subjects, simultaneous blood hormone assays were also performed. The results showed that the viscoelasticity of sublingual saliva parallels that of cervical mucus, in all cases; with the highest fluidity occurring at midcycle at the time of the estradiol surge. In the ovulating woman, typical confirmatory patterns are seen in all of the measurements.

Figure 3A:
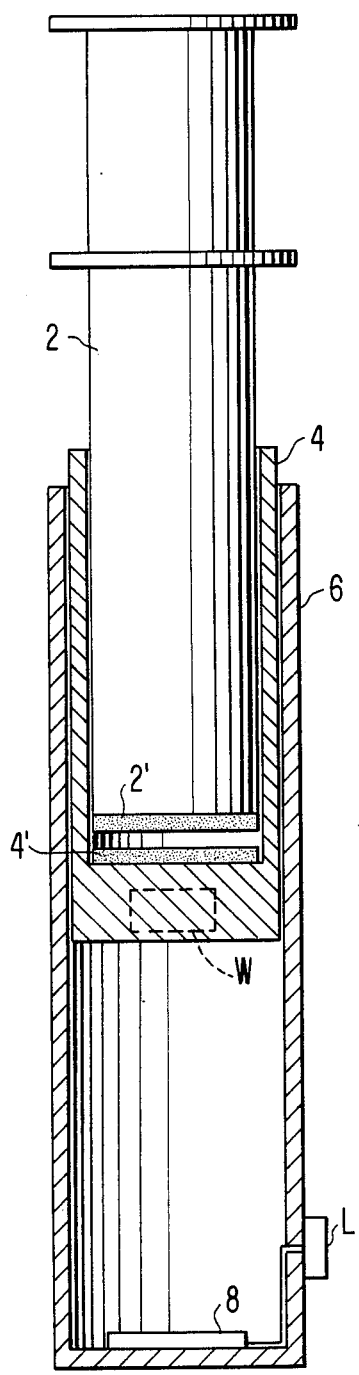
FIG. 3A is a longitudinal section of a simple ovulation monitor instrument for using the technique of the invention.

A very simple instrument for universal and inexpensive use, including adaptability for throw away after a use if desired, is shown in FIG. 3A upon a somewhat enlarged scale—the instrument being constructable in dimensions commensurate with a narrow syringe. The plunger 2, such as a glass piston, or other sample carrier, is provided with a saliva sample surface 2', roughened as before discussed finely enough to cause adhering of the saliva when the plunger 2 is removed and placed under the tongue to extract a sample (much as in using oral thermometers). The plunger is then inserted, as shown, within a recessed or re-entrant coaxial cylindrical tube 4, the outer walls of which are fitted within an outer coaxial cylinder 6 and with either a fractional fit or a detent or the like holding the tube 4 in elevated position, as shown, in the outer cylinder 6. At the bottom of the recess of cylinder is an opposing roughened surface 4' similar to the surface 2' and between which and the surface 2' the saliva sample is compressed when the plunger 2 is inserted down into the recess of the cylinder 4. Fastened to the bottom of the cylinder 4 is a predetermined weight W (shown embedded in the cylinder base) adjusted to be sufficient to cause the cylinder 4 to separate from the plunger 2 and to drop, under the influence of gravity, to the bottom of the outer cylinder 6 in the event that the viscoelasticity of the saliva sample is not sufficient to hold the cylinder 4 elevated, and to prevent fracture under the pulling or stretching force of the weight (as when the viscoelasticty dips toward S of FIG. 1). The weight may be of the order of 5 grams, calibrated by the physician.

The striking of the bottom of the cylinder 4 against an electrical contact or switch 8 at the base of the outer cylinder 6 may complete a circuit containing a miniature battery and control the activation of an indicator lamp L carried by the cylinder 6. If the light goes on, this is an indication to the woman of the near or substantial coincidence of the thusly measured degree of saliva viscosity with the time of the dipping characteristic; and she can take advantage of the up-coming ovulation for fertilization or the converse.

Figure 3B:
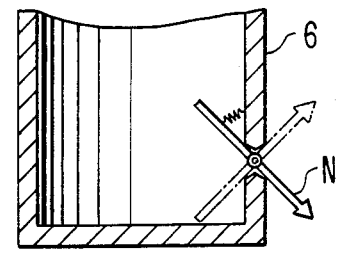
FIG. 3B is a similar fragmentary view of a modification.

Alternatively, a less expensive pivotable spring-retained needle indicator N may be provided, as shown in FIG. 3B, as may other indicating devices be employed as well.

For non-ovulating cycles, as in the case of women taking birth control pills, the salivary viscoelasticity does not show this characteristic ovulatory deep dip S, but rather remains elevated throughout the cycle.

The invention thus enables an immediate and reliable assessment of the ovulatory and concomitant hormonal status of the patient as destermined in her saliva, without the necessity for vaginal intrusion or blood sampling.

Further modifications will occur to those skilled in the art, including the use of other types of rheometers, and such are considered to fall within the spirit and scope or the invention as defined in the appended claims.

What is claimed is:

1. A process for determining the time of ovulation of a female, that comprises, extracting a sample of sublingual saliva from the mouth of the female; compressing the sample between opposing surfaces adapted to cause adherence of the saliva to the same; applying a predetermined relative force between said surfaces to stretch the saliva, the amount of stretching of the saliva providing a measure of the degree of viscoelasticity of the saliva under such predetermined force; and providing an indication if there is near and substantial coincidence of the measured degree of viscoelasticity with a predetermined unique monthly minimum dip of viscoelasticity in the sublingual saliva of the female to identify that the time of midcycle of ovulation is about to occur.

2. A process as claimed in claim 1 and in which the saliva of the female is observed to determine said minimum dip of viscoelasticity and said predetermined force is adjusted to cause fracture of the sample when the viscoelasticity decreases in said dip.

3. A process as claimed in claim 2 and in which said force is calibrated to provide up to 48 hours of indication for purposes of determining optimum fertility.

4. A process as claimed in claim 1 and in which the sample is of the order of 0.25 mm in thickness.

5. Ovulation indicating apparatus having, in combination, plunger means provided with a finely roughened end surface insertable in the mouth to coat the surface with an adhering sublingual saliva sample; means comprising a re-entrant tube disposed within a coaxial cylinder for receiving the plunger means, said receiving means having an opposing roughened bottom surface against which the sample carried by the plunger means end surface is to be compressed; and means comprising a calibrated weight carried by said tube for applying a force between the roughened surfaces to stretch the compressed saliva sample, the force-applying means being calibrated to produce a predetermined force equal to that required to cause fracture of the sample and separation of said plunger means and said tube when the viscoelasticity of the sample substantially coincides with a predetermined unique monthly minimum dip in sublingual saliva viscoelasticity, said cylinder having means operating as a result of the separation of said plunger means and said tube for indicating such fracture of the sample to enable intercourse abstinence or activity.

6. An ovulation indicating apparatus as claimed in claim 5 and in which said indicating means includes an indicator and means disposed near a bottom of the cylinder for activating the indicator upon dropping of the tube within the cylinder.

7. A process for determining the time of ovulation of a female, comprising the steps of extracting a sample of sublingual saliva from the mouth of the female; compressing the sample between a pair of opposed surfaces conditioned to cause adherence of the saliva to the surfaces; stretching the sample between the two surfaces with a predetermined force, the amount of stretch in response to said predetermined force providing a measure of viscoelasticity of the sample; and ascertaining whether the measure of viscoelasticity substantially coincides with a predetermined unique monthly minimum dip of viscoelasticity in the sublingual saliva of the female.

8. A process as claimed in claim 7 and in which the substantial coincidence of the measure of viscoelasticity with the predetermined monthly minimum dip is ascertained by providing an observable indication of such coincidence.

9. A process as claimed in claim 8 and in which said indication is visibly observable.

10. A process as claimed in claim 8 and in which said indication is provided as a result of separation of said two surfaces.

* * * * *